United States Patent [19]

Bruce

[11] Patent Number: 4,997,961

[45] Date of Patent: Mar. 5, 1991

[54] COMPOUNDS OF THE ANTHRAQUINONE SERIES

[75] Inventor: John M. Bruce, Wilmslow, England

[73] Assignee: The Victoria University of Manchester, Manchester, England

[21] Appl. No.: 484,572

[22] Filed: Feb. 26, 1990

Related U.S. Application Data

[63] Continuation-in-part of Ser. No. 377,835, filed as PCT GB88/00912 on Oct. 21, 1988, published as WO89/03822 on May 5, 1989, Pat. No. 4,927,845.

[30] Foreign Application Priority Data

Oct. 22, 1987 [GB] United Kingdom ............... 8724799
Oct. 22, 1987 [GB] United Kingdom ............... 8724800

[51] Int. Cl.$^5$ .......................................... C07C 149/36
[52] U.S. Cl. .................................. 552/289; 552/290
[58] Field of Search ............................. 552/289, 290

[56] References Cited

FOREIGN PATENT DOCUMENTS 2495934 6/1987 France ............................... 514/480

OTHER PUBLICATIONS

Synthesis, Journal of Synthetic Organic Chemistry, No. 5, May 1986 (Stuttgart DE), M.d'Ischia et al.: "Synthesis of 10-Alkylthio-and Arylthio-1,8-Dihydroxy-9-Anthrone, a New Class of Anthracene Derivatives of Potential Pharmacological Interest", pp. 430–431.

Primary Examiner—Richard L. Raymond
Assistant Examiner—Raymond Covington
Attorney, Agent, or Firm—Cushman, Darby & Cushman

[57] ABSTRACT

Anthralin analogues containing a thio-substituent, especially in one or more of the positions 2-, 7- and 10- of the anthralin ring. They may be made by reacting an anthralin derivative (e.g. 10-bromoanthralin) with a thiol or a compound containing a group convertible to a thio-group. Alternatively, a 1,8-dihydroxy anthraquinone containing a thio-substituent may be reduced. Reactive intermediates may be made by introducing one or more nuclear allylic groups into a 1,8-dihydroxy anthraquinone and then converting them into a reactive form, e.g. by epoxydation or halide addition. The intermediate can then be reduced to the oxidation state corresponding to anthralin.

Additional compounds, having the 10-carbon atom of the anthralin ring as part of a heterocyclic ring, may be made by oxidising anthralins containing various substituted thioalkyl groups as the 10-substituent.

The compounds are useful for treatment of psoriasis, and may be formulated in the conventional vehicles for topical application, especially petrolatum.

3 Claims, No Drawings

COMPOUNDS OF THE ANTHRAQUINONE SERIES

This application is a continuation-in-part of Ser. No. 07/377,835, filed as PCT GB88/00912 on Oct. 21, 1988, published as WO89/03822 on May 5, 1989 now U.S. Pat. No. 4,927,845.

This invention relates to new compounds of the anthraquinone series which are useful in the treatment of psoriasis.

It has been well known for many years that the compound known as anthralin (dithranol, or 1,8-dihydroxy-9-anthrone) is useful for the topical treatment of psoriasis. While this compound is effective, however, it has the strong disadvantages of also causing staining and irritation. Staining of the skin normally clears within about four weeks after treatment ceases, but the staining also affects bed linen, clothing, and equipment, and so is a major drawback in practical use in many senses, especially to out-patients.

Irritation is a major drawback which can be sufficiently severe as to require treatment to be discontinued for about 10% of patients for whom anthralin therapy would otherwise be appropriate. The staining is not only objectionable to the patients, but also is difficult to remove from fabrics and bathroom fittings.

Accordingly, there is a great need for a treatment agent which does not have these disadvantages.

We have now found that these disadvantages can be reduced by a modification of the structure of the anthralin molecule.

Thus according to our invention we provide new organic compounds, useful for the treatment of psoriasis, which are analogues of anthralin having a thio substituent in the molecule.

Alternatively, these compounds can be described as 1,8-dihydroxy-9-anthrones having a thio substituent in the molecule.

The thio substituent may be present in any position in the anthralin molecule, but it is easier to establish it in some positions than in others. Thus, the positions in which it can be built into the molecule are mainly determined by the ease of providing a reactive centre through which the thio substituent can be attached, and consequently it is preferred that it be attached in one or more of the positions 2, 7 and 10 in the anthralin ring system, and especially in position 10.

We are aware of the publication by d'Ischia and Prota (Synthesis, A Journal of Synthetic Organic Chemistry, No. 5, May 1986, pages 430–431) in which four specific compounds are disclosed, which are 10-thio derivatives of anthralin, and we make no claim herein to any compound disclosed in that reference. It is noted that the publication identifies no use or pharmaceutical activity for any of the said compounds described therein, except for the well-known activity of anthralin itself.

Thus we provide, as new compounds, 10-thiosubstituted derivatives of anthralin wherein the 10-thio substituent is other than the 10-butylthio-, 10-phenylthio-, 10-benzylthio- or the 10-(2-amino-2-carboxy-ethyl)thio- substituents.

Thus according to our invention we provide new organic compounds, useful for the treatment of psoriasis, which are analogues of anthralin containing a thio-substituent in the molecule, with the exception of the 10-phenylthio-, 10-butylthio-, 10-benzylthio- and 10-(2-amino-2-carboxy-ethyl)thio- derivatives of anthralin.

Especially we provide new compounds which are analogues of anthralin containing a thio-substituent in the molecule, and in which the thio-substituent is in the 10-position of the anthralin ring and is of the structure:

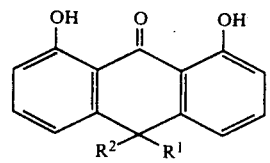

wherein
$R^1$ represents the substituent —SR, wherein R represents:
  (a) an alkyl group of 1 to 3 carbon atoms; or
  (b) an alkyl group of 5 to 12 carbon atoms; or
  (c) an alkyl group of 1 to 12 carbon atoms substituted by one or more of the groups —COOH (or an ester thereof), —OH, —SH or a thiocarbamate group for example —S.CO.NH.Phenyl; or
  (d) a substituted aryl group; or
and
$R^2$ represents hydrogen or $R^1$ (in which case the two groups R therein may be the same or different), $R^1$ and $R^2$ together with the carbon atom of the 10-position of the anthralin ring form a group of the structure:

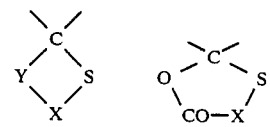

wherein Y represents an oxygen atom (O) or a sulphur atom (S), and X represents a linking group, for example a methylene or polymethylene group, especially —CH$_2$— or —(CH$_2$)$_2$—.

The term "thio substituent" is used herein to mean a substituent containing a sulphide linkage (i.e. a C—S linkage, especially a C—S—C or a C—SH linkage) and does not include substituents in which the sulphur is in an oxidised state, as for example in sulphoxides, sulphones or sulphonic acids.

Such thio substituents may take a wide variety of different forms. Most conveniently, it may be part of a larger group containing the sulphur bound in as indicated above but as a small part of the structure. This allows for adjusting the properties of the molecule as a whole and, in some instances, better stability or ease of manufacture.

In general it is possible to make the products of the invention by various routes, according to the ease of obtaining the desired starting materials.

According to the invention we provide a method for the manufacture of analogues of antralin having a thio substituent in the molecule, which comprises interaction between a thiol and an anthralin containing a substituent which is reactive towards the thiol to form a sulphur-containing molecular link.

The substituent which is reactive towards the thiol to form a thio (i.e. sulphur-containing) link may be especially in one or more of the positions 2, 7 and 10 in the anthralin ring system, and especially in the 10-position.

There are two main variants of this method. One starts from the thiol and a derivative of anthralin containing a substituent which is reactive towards the thiol, so that the desired product containing a sulphide (C—S—C) bond is obtained directly. The other is to use a derivative of anthralin containing a reactive group and react this with a compound which, though not itself containing a thiol group, contains a group which is convertible to a thio group.

When the reactive group is attached directly to a carbon atom of the anthralin ring system, this method is applicable to making 10-substituted anthralin derivatives, because nucleophilic substitution of the anthralin ring can be made to take place most readily in the 10-position. Thus, the procedure may start from a 10-halogenated anthralin (a 10-halogenated 1,8-dihydroxy-9-anthrone). The halogen atom may be any which imparts an appropriate degree of reactivity, consistent with reasonable stability; it is preferably bromine, as in 10-bromoanthralin, but other halogens may be used if desirable.

This halogen atom may then be used for reaction with either a thiol (i.e. to form a sulphide link directly) or with another compound which, though not itself containing a sulphide link can be converted by a further stage of reaction into such a compound (i.e. to form a sulphide link indirectly). The reaction of the 10-halogenated anthralin with a compound containing a thiol group gives a product containing the sulphur atom attached to the 10-position of the anthralin ring.

When the sulphur-containing part of the molecule is introduced by building on to reactive groups present in the substituents and is not attached directly by a C—S bond to a carbon atom of the anthralin ring system, this method may be employed regardless of the particular position the substituent occupies in the anthralin ring system. It is especially useful for making products substituted in the 2-position or in the 2-and 7-positions of the anthralin ring system, but can also be used to make products substituted in the 10-position of the anthralin ring system.

The reaction may be carried out in the manner conventional for the reaction of thiols with reactive halogen-containing compounds. It is particularly convenient to carry it out in the presence of a solvent, for example a halogenated hydrocarbon solvent: A very suitable and convenient solvent is dichloromethane, especially as this is a good solvent for 10-bromo-anthralin. The reaction is usually carried out easily by mixing the reactants and stirring them together at ambient temperature, though the reaction may in some cases be assisted by heating.

According to the invention we also provide a method for the manufacture of analogues of anthralin having a thio substituent in the molecule, which comprises reducing a 1,8-dihydroxy-9,10-anthraquinone which contains a thio substituent in the molecule.

The reducing agent for this purpose may be any which will reduce the 10-carbonyl group to methylene, so reducing the 9,10-anthraquinone structure to the corresponding 9-anthrone structure, without adversely affecting the rest of the molecule and especially without removing the sulphur of the thio group.

Examples of suitable reagents include tin and hydrochloric acid, aluminium and sulphuric acid, and other dissolving metal systems.

The method is especially applicable to the production of compounds having substituents in the 2-position or the 2- and 7-positions of the anthralin ring system, and the main step is that of introducing the substituent into the ring system.

This can be carried out very conveniently in two stages comprising:

(1) introducing an allylic substituent into a compound having the carbon ring system of anthraquinone, and (2) subjecting this allylated compound to chemical reaction which converts the allylic substituent into a thio-bearing substituent, and converting the anthraquinone ring system to the oxidation state appropriate for the anthralin system.

This uses the reactivity of the allylic double bond to provide the point of attachment or formation of the sulphur linkage required for the thio substituent, and the greater suitability of the hydroxyanthraquinone for the introduction of a substituent.

The sequence of the two parts of stage (2) above is most conveniently as mentioned above, to avoid carrying them out in a way which results in one stage destroying the results of a previous one.

This method based on allylation forms those anthralin derivatives containing at least three carbon atoms in the substituent, and having the sulphur atom of the thio group attached to a carbon atom of the side-chain.

The 2-substituted and 2,7-di-substituted 1,8-dihydroxy anthraquinones required for this process may be made by allylating a 1,8-dihydroxy 9,10-anthraquinone. This may be achieved by treating the 1,8-dihydroxy 9,10-anthraquinone with an allylating agent.

This process results overall in allylation of the anthraquinone structure in positions adjacent to the hydroxyl substituents. The allylation reaction leads first to a product in which one or both of the 1- and 8-hydroxy groups are converted to allylic ether groups. The transfer of the allylic group from the ether oxygen to the adjacent carbon atom (the 2 and 7-carbon atoms respectively) of the anthraquinone ring structure can then be achieved by the reaction known as a reductive Claisen rearrangement.

The allylating agents which may be used for this purpose are compounds containing the carbon structure of the allyl group, i.e. C=C—C—. These agents have the structure C=C—C—X, wherein X represents a reactive atom or group, especially a halogen atom. The halogen atom may be any which imparts an appropriate degree of reactivity to the allylating agent, consistent with reasonable stability; usually it is preferably bromine, but if desired it may chlorine or iodine.

The simplest allylating agent compound is an allyl halide, for example allyl bromide. Substituted derivatives of the simple allyl compounds can also be used, for example those wherein one or more of the valence positions in the allylic group (C=C—C—) are hydrocarbon groups. Examples of these include methallyl halides, which have the structure $CH_2=CH(CH_3)—CH_2—Halogen$.

The reaction conditions for the allylation are those conventional for ether formation from phenolic hydroxy compounds, for example reaction between the hydroxy compound and the allylating agent in the presence of a base, and preferably also in the presence of a solvent or diluent. The reductive Claisen rearrangement, to convert the allylic ether to the derivative with the allylic substituent in the anthraquinone ring, may be carried out by treatment of the allylic ether derivative with an aqueous solution of alkaline dithionite (for example alkaline sodium dithionite).

Direct allylation of the 1,8-dihydroxy-9,10-anthraquinone leads to a product which contains the di-ether and the mono-ether in proportions which depend upon the reaction conditions used, and the mono and di ethers may be separated if desired. This route, using an excess of allylating agent, is therefore preferred for making the 2,7-di-allylated product.

When the mono-allylated product is desired as the principal product, the preferred procedure is to allylate a 1,8-dihydroxyanthraquinone in which one hydroxyl group is protected, for example by etherification. This protection is achieved by a group which can be removed easily after the allylation of the other hydroxyl group has been carried out. Conveniently, for example, this may be done by using a derivative of 1,8-dihydroxy anthraquinone in which one of the hydroxyls is replaced by an alkoxy group, most conveniently a methoxy group. Thus, a 2-allylated 1-hydroxy-8-alkoxy-9,10-anthraquinone required as starting material for making a 2-substituted anthralin may be made by allylating the corresponding 1-hydroxy-8-alkoxy-9,10-anthraquinone in a manner analogous to that described above for allylating a 1,8-dihydroxy-9,10-anthraquinone. The allylated product (a 2-allylated 1-hydroxy-8-alkoxy-9,10-anthraquinone) can then be de-alkylated to free the 8-hydroxy group and form a 2-allylated 1,8-dihydroxy-9,10-anthraquinone. For this purpose, convenient de-alkylating reagents include hydrogen bromide in acetic acid, and a thiolate (especially an alkyl thiolate, for example sodium ethyl thiolate), conveniently in a dipolar aprotic solvent, for example dimethylformamide.

It is very convenient to have the reactive group situated in a larger substituent in the anthralin ring system, as this allows a greater range of structures to be formed. For example, a variety of reactive groups may be introduced by first forming an anthralin ring structure containing an allylic substituent, and then using this allylic substituent to form the desired reactive group. An example of this is the treatment of the compound containing the allylic group with a reagent which converts the ethylenic double bond into a group reactive towards thiols.

In particular, the ethylenic double bond may be reacted with a halogen or a hydrogen halide so as to introduce a halogen atom, which can then be used to react with a thiol. This addition may be carried out in any manner known in the art, for example the hydrogen bromide addition can be carried out in solution in acetic acid. The reaction with hydrogen bromide is especially convenient as it can be carried out on a 2-allylated 1-hydroxy-8-alkoxy-9,10-anthraquinone (mentioned above as a convenient intermediate for making a mono-allylated product) to bring about both the de-alkylation and the addition at the ethylenic double bond.

Another method is to convert the ethylenic double bond into an epoxy group (by treatment with a reagent known for this purpose) and then using this epoxy group to react with a thiol, thus forming thioether alcohols. The epoxidation can be carried out in the manner known in the art, for example by the action of per-acids. Epoxy compounds react with a thiol (RSH) to form a hydroxylated sulphide substituent, of which two isomers are obtainable and usually a mixture of both is obtained.

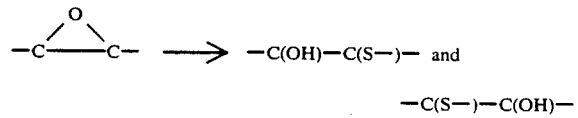

Similarly, reaction of a thiol (RSH) with a bis-epoxide - for example that obtained by epoxidation of 2,7-bis-allyl 1,8-dihydroxy anthraquinone—can lead to three isomeric hydroxy-thio products.

For any of the reactions indicated above as requiring a thiol, the thiol can be any thiol. It may be for example a thiol of the formula R—SH, wherein R represents a hydrocarbon group or substituted hydrocarbon group, which may be either a saturated or unsaturated hydrocarbon group, especially an alkyl or alkenyl group or a substituted alkyl or alkenyl group. Such hydrocarbon groups may be straight-chain, branched, cyclic, and aliphatic, araliphatic or aromatic in nature. Examples include methyl, ethyl, propyl, phenyl, benzyl, allyl, methallyl, and their derivatives and analogues. Likewise, R may represent a heterocyclic group or a substituted heterocyclic group. Any of these may be substituted, for example by halogen, hydroxyl, etc..

Alternative forms of thiol are those compounds which contain the thiol group (—SH) and also further functional or reactive groups.

Examples of such compounds include:
(a) mercapto-alkanoic acids and their esters;
(b) mercapto-alkanols and mercapto-phenols;
(c) poly-mercapto compounds, e.g. bis-mercapto alkanes;
(d) thiols containing a basic substituent, for example amino, alkylamino or heterocyclic substituents.

These further functional groups (amino, carboxylic, hydroxyl, etc.,) present in the molecule offer the advantage of contributing to the control or manipulation of the properties of the compound, especially its ionic character, solubility and the like, which can then contribute to its formulation and therapeutic effectiveness. Thus, mercapto-alkanoic esters can be hydrolysed and provide an alternative route to the free carboxylic acid form, and mercapto-alkanols and mercapto-alkanoic acids (and their esters) can provide a site for further reaction. For example, a carboxylic group can be converted to the acid halide to enhance its reactivity for binding on any further desired structural elements. Conventional reagents may be used, for example oxalyl chloride can convert a carboxylic acid group to the acid chloride.

The product may contain more than one sulphur linkage if desired, for example by using a polythiol [(c) above] or by using a reactive group in the thio substituent to build in a further sulphur-containing structure, or by using a bis-allylated derivative and developing both allylic groups into thio substituents. Similarly, the molecule may contain more than one anthralin ring system, as for example by linking two (or more) anthralin rings by way of a thio linkage, or by linking two (or more) anthralin rings each containing the desired thio substituents.

An especially desirable form of thio substituent is one which contains latent basic properties, i.e. the ability to liberate a base by decomposition or hydrolytic cleavage, especially if this can occur in vivo. This is because the anthralin radical moiety is believed to be the effective agent in the therapeutic activity of anthralins, and the formation of the enolate form of the anthralin moiety is believed to be a more facile source of the corresponding anthralin radical. One example of this is the use of an amino thiol [(d) above], as the reaction to the initial formation of the anthralin derivative as a salt of the basic form, which is more stable than the free base form. Another example is a compound containing a thiocarbamate group, which can break down to liberate the thiol and also free amine (derived from the isocyanate used for preparing the thiocarbamate from the corresponding thiol). The amine, by producing basic conditions, can thus provide a built-in source of basic activation for the anthralin moiety. A thiocarbamate may be made by treating a compound containing a free thiol group with an isocyanate.

According to a further feature of our invention we provide new organic compounds, useful for the treatment of psoriasis, which are analogues of anthralin containing a structure at the 10-position of the anthralin ring system which locks the structure of the molecule in the non-enolic form and does not permit isomerisation to the enolic form.

Especially, such compounds contain the sulphur atom of the thio-substituent attached to the 10-carbon atom of the anthralin ring, as part of a heterocyclic ring.

This fixation of the molecular structure can be achieved by forming a "spiro" derivative in which the 10-carbon atom of the anthralin ring system becomes part of a heterocyclic ring by utilising both valencies of the 10-carbon atom which are not taken up in the anthralin ring formation.

Such new compounds can be made by oxidising anthralin derivatives containing one hydrogen atom and a substituent R at the 10-position of the anthralin ring system, wherein R represents a substituent which can cyclise back on to the 10-carbon atom to form a stable ring system incorporating the 10-carbon atom of the anthralin structure.

Examples of the substituent R include:
—S—(CH$_2$)$_n$—CH$_2$OH, —S—(CH$_2$)—CH$_2$SH and —S—(CH$_2$)—COOH,
wherein n has the meaning indicated below.

By oxidation the compounds containing these substituents cyclise to form ring systems as follows:

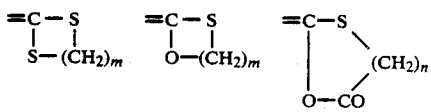

wherein n represents an integer, preferably in the range 1 to 3 (for example 2) but may be larger if desired, and m represents an integer equal to n+1.

These compounds contain a sulphur atom attached to the 10-position of the anthralin ring system.

The thiol, as required for the purposes of this process, is a compound of the structure HS-X-Y, wherein Y represents a reactive group capable of effecting the desired ring closure and X represents a divalent linking group.

The reactive group Y may conveniently be a hydroxymethyl group (CH$_2$OH), a mercapto group (SH) or a carboxylic group (COOH) or a functional derivative thereof.

Examples of such compounds include:
(a) mercapto-alkanoic acids and their esters;
(b) mercapto-alkanols;
(c) poly-mercapto compounds, e.g. bis-mercapto alkanes.

The linking group X should be one which facilitates the formation of the desired second ring system, and is preferably a polymethylene group, for example an ethylene or a trimethylene group, though it may contain more or less methylene groups if desired, and these may optionally be substituted.

The oxidising agent may be one which acts by single electron transfer, and may be an organic oxidant, for example a quinone (especially 2,3-dichloro-5,6-dicyano-1,4-benzoquinone) or an inorganic oxidant for example tetravalent cerium (Ce$^{IV}$).

The compounds required for use as starting materials for this process may be made by interaction between a thiol (as defined above) and an anthralin containing a substituent in the 10-position which is reactive towards the thiol to form a sulphur-containing molecular link.

Thus, the procedure may start from a 10-halogenated anthralin (a 10-halogenated 1,8-dihydroxy-9-anthrone). The halogen atom may be any which imparts an appropriate degree of reactivity, consistent with reasonable stability; it is preferably bromine, but other halogens may be used if desired.

The reaction may be carried out in the manner conventional for the reaction of thiols with reactive halogen-containing compounds. It is particularly convenient to carry it out in the presence of a solvent, for example a halogenated hydrocarbon solvent, and most conveniently a chlorinated hydrocarbon solvent. A very suitable and convenient solvent is dichloromethane, especially as this is a good solvent for 10-bromo-anthralin. The reaction is usually carried out easily by mixing the reactants and stirring them together at ambient temperature, though higher or lower temperatures may be used if desired.

In use, the compounds of the invention may be formulated most conveniently in any form which is appropriate for topical application, for example into ointment form, for example in petrolatum—alone or in conjunction with adjuvants which enhance their stability or assist their absorption into skin tissue.

The invention also provides pharmaceutical compositions for use in anti-psoriatic therapy, comprising at least one compound of this invention together with one or more pharmaceutical carriers or excipients. Such compositions may be in any forms adapted for topical administration.

The active compounds of this invention may advantageously be formulated in conventional manner into preparations suitable for topical administration with the aid of a topical vehicle therefor.

Examples of various types of preparation for topical administration include ointments, lotions, creams, powders and the like, but those of an ointment or cream form are preferred.

The role of the components in the formulation may be to help the active compound enter the skin or it may be to help retain the active agent at the desired treatment site and minimise any undesired migration or wastage.

Ointments or creams may, for example, be formulated with an aqueous or oily base with the addition of suitable thickening and/or gelling agents and/or solvents. Such a base may thus include water and/or an oil such as liquid paraffin or a vegetable oil such as arachis oil or castor oil, or a solvent such as a polyethylene glycol having an average molecular weight in the range 200–600. Thickening agents which may be used according to the nature of the base include soft paraffin, aluminium stearate, cetostearyl alcohol, polyethylene glycols of an average molecular weight in the range 4000–6000, woolfat, and beeswax and/or glyceryl mono-stearate and/or non-ionic emulsifying agents, and mixtures or combinations thereof.

The proportion of the active compound of the invention in the topical compositions according to the invention depends upon the precise type of formulation to be prepared and the particular needs of individual patients but will generally be in the range from 0.001% to 25% by weight of the total formulation, but larger or smaller proportions may be used if desired—even up to 90% or more. Generally, however, for most purposes the proportion used will be in the range from 0.01% to 10%, and preferably in the range from 0.1% to 5%. It is not practicable to specify any precise formulation suitable for all purposes, as the treatment of psoriasis is very variable, and the procedures and the strength of any formulations used are very dependent upon the particular patient's sensitivity and reaction, the severity or type of psoriasis involved, and the stage in the treatment. It is common, for example, to treat a patient initially with a formulation having a low concentration of active agent, and then to increase the concentration of active agent progressively in formulations applied later, according to how the patient responds and whether the treatment is by applications of long or short duration.

The duration of treatment may vary widely, from minutes to hours, and the treatments may be from one to several times a day. The treatment of the present invention may also be used alone or in conjunction with other treatments, for example removal of the treatment agents by washing, application of soothing or emollient creams or lotions, irradiation with ultraviolet light, and combinations of these. The choice will depend upon the results of simple trial by the therapist in response to observation of the extent to which the patient shows benefit.

For example, the formulations may contain other active ingredients or ancillary additives, for example preservatives.

Much of the detail of conventional anthralin therapy, which can be used as guidance for utilisation of the present invention, is described more fully in a variety of textbooks, for example in "Psoriasis," edited by H. H. Roenigk and H. I. Maibach, (published by Dekker, 1985), "Textbook of Psoriasis," edited by P. D. Meir and P. C. M. van de Kerkhof (published by Churchill Livingstone, 1986) and "The Chemotherapy of Psoriasis," edited by H. P. Baden, (published by Pergamon, 1984).

The invention is illustrated but not limited by the following Examples in which the parts and percentages are by weight unless otherwise stated.

EXAMPLE 1

Preparation of
1,8-Dihydroxy-10-Phenylthio-9-Anthrone.

1-Bromo-1,8-dihydroxy-9-anthrone (3.05 g) was dissolved in dichloromethane (100 ml) and thiophenol (1.1 ml) was added. The red-brown solution became yellow-green, and was then left, with stirring, at room temperature for 5 hours. Removal of the solvent gave a yellow solid which, after recrystallisation from a hexane/chloroform mixture (10:1), afforded 1,8-dihydroxy-10-phenylthio- 9-anthrone (2.89 g, 87%) as pale yellow needles, melting point 156°–157° C. (Found: C 71.8, H 4.2, S 9.95; $C_{20}H_{14}O_3S$ requires C 71.85, H 4.2, S 9.6%.)

Physical properties measured:
delta ($CDCl_3$, 220 MHz) 5.43 (s, H-10), 6.75 (dd, $J_1$=7.5, $J_2$1.5, H-2'+H-6'), 6.90 (d, J=7.5, H-2 +H-7), 7.02 (d, J=7, H-4 +H-5), 7.13 (t, J=7, H-3'+H-5'), 7.34 (bt, J=7, H-4'), 7.51 (t, J=7, H-3+H-6), 11.83 (s, 1—OH +8—OH); nu max. (film), 1629s, 1598vs, 1483m, 1448m, 1273vs, 1215s, 750vs cm$^{-1}$; and m/z EI 334 (M$^+$, 3.3), 333 [(M-1)$^+$, 5.1], 300 [(M-34)$^+$, 3.7], 226 [(Anthralin)$^+$, 30.7], 225 [(M-SPh)$^+$, 100], 198 [(Anthralin-CO)$^+$, 7.3], 197 [(M-SPh-CO)$^+$, 38], 110 (PhSH$^+$, 14.6), 109 (PhS$^+$, 7.9).

EXAMPLE 2

Preparation of
1,8-Dihydroxy-10-Ethylthio-9-Anthrone.

10-Bromo-1,8-dihydroxy-9-anthrone (3.05 g) was dissolved in dichloromethane (100 ml) and ethanethiol (1 ml) was added. The solution was left stirring at room temperature for 6 hours, during which time the red-brown solution became yellow-green Removal of the solvent gave a yellow solid which, recrystallised from hexane, gave 1,8-dihydroxy-10-ethylthio-9-anthrone (2.63 g, 91%) as bright yellow needles, melting point 117°–118° C.

(Found: C 67.3, H 5.1, S 11.1; $C_{16}H_{14}O_3S$ requires C 67.1, H 4.93, S 11.2%.)

Physical properties measured:
delta ($CDCl_3$, 220 MHz) 1.01 (t, J=7.5, Me), 2.21 (q, J=7.5, —$CH_2$—), 5.19 (s, H-10), 6.95 (d, J=8.5, H-2+H-7), 7.13 (d, J=7.8, H-4+H-5), 7.53 (t, J=8, H-3+H-6), 12.13 (s, 1—OH +8—OH);

nu max. (film), 1628s, 1600vs, 1482s, 1448s, 1274vs, 1213s, 1154m, 1072m, 836sh, 752vs, 736s, 718s cm$^{-1}$; and m/z EI 286 (M$^+$, 4.7), 257 [(M-Et)$^+$, 1.9], 256 [(M-1-Et)$^+$, 1.9], 226 [(Anthralin)$^+$, 64.1], 225 [(M-SEt)$^+$, 100], 198 [(Anthralin-CO)$^+$, 15.2], 197[(M-SEt-CO)$^+$, 47.4], 62 (EtSH$^+$, 37.9].

EXAMPLE 3

Preparation of
1,8-Dihydroxy-10-Hexylthio-9-Anthrone

10-Bromo-1,8-dihydroxy-9-anthrone (91.5 mg) was dissolved in dichloromethane (10 ml) and the solution was purged with nitrogen for 10 minutes. 1-Hexanethiol (0.05 ml) was then added and the solution was stirred at room temperature for 3 days under nitrogen. Removal of the solvent gave a yellow sticky solid which was a mixture of 1,8-dihydroxy-10-hexylthio-9-anthrone, 1,8-dihydroxy-10,10-dihexylthio-9-anthrone, anthralin and tetrahydroxy-dianthrone in the ratio 13:1.5:1:1.3 respectively, from the integrals of the four different hydroxyl group resonances in the nmr spectrum.

The mixture (60 mg) was separated by silica gel plc using a mixture of petroleum ether (boiling point 40°–60° C.) and ethyl acetate (4:1).

The first band was isolated as a yellow oil (7 mg) which may be 1,8-dihydroxy-10,10-dihexylthio-9-anthrone Physical properties measured:
delta ($CDCl_3$, 60 MHz), 0.7-1.5 [m, 2x—($CH_2$-)$_4$—$CH_3$], 2.0–2.3 (m, 2x—$SCH_2$—), 6.27 (dd, $J_1$=8, $J_2$=1.5, H-2+H-7 or H-4+H-5), 7.5 (t, J=8, H-3+H-6), 7.77 (dd, $J_1$=8, $J_2$=1.5, H-4+H-5 or H-2+H-7), 12.38 (s, 1—OH +8—OH); and m/z EI 458 (M+, very small), 341 [(M-S(C$_6$H$_{13}$)+, 56.3], 257(66.5), 256[(M-SC$_6$H$_{13}$)+, 26.4], 226 [(Anthralin)+, 24], 225 [(Anthralin-1)+, 80], 19.7 [(Anthralin-1-CO)+, 42.2], 117 [(HSC$_6$H$_{13}$)+, 5.6].

The second band was isolated and recrystallised from hexane to give the major component, 1,8-dihydroxy-10-hexylthio-9-anthrone (41 mg, 61%) as pale yellow needles, melting point 49°-50° C.

(Found: C 70.4, H 6.7, S 9.3; C$_{20}$H$_{22}$O$_3$S requires C 70.1, H 6.5, S 9.35%).

Physical properties measured:

delta (CDCl$_3$, 220 MHz) 0.79 (t, J=7, CH$_3$), 1-1.35 [m, —(CH$_2$)$_4$—9 , 2.14 (t, J=7, —SCH$_2$—), 5.17 (s, H-10), 6.93 (d, J=8.3, H-2+H-7), 7.12 (d, J=7.5, H-4+H-5), 7.53 (t, J=8, H-3+H-6), 12.14 (s, 1—OH+-8—OH);

nu max. (film), 2956m, 2926s, 2855m, 1632s, 1613vs, 1600vs, 1485s, 1448vs, 1293s, 1279vs, 1221s, 1185m, 1073w, 921w, 838sh, 744s cm$^{-1}$; and m/z EI 342 (M+, 1.3), 341 [(M-1+, 1], 257 [(M-C$_6$H$_{13}$)+, 5.5], 256((5.5), 226 [(Anthralin+, 52.3], 225 [(M-SC$_6$H$_{13}$)+, 100], 197 [(M-SC$_6$H$_{13}$—CO)+, 68.2], 118(6.2), 117(3.4), 85(18.7), 84(12.6).

The third band was isolated to give 1,8-dihydroxy-9-anthrone (5 mg) as a yellow solid.

Physical properties measured:

delta (CDCl$_3$, 60 MHz) 4.24 (s, 2×H-10), 6.83 (bd, H-2+H-4+H-5+H-8), 7.45 (dd, H-3+H-6), 12.19 (s, 1—OH+8—OH).

EXAMPLE 4

Preparation of 1,8-Dihydroxy-10-Dodecylthio-9-Anthrone.

10-Bromo-1,8-dihydroxy-9-anthrone (75 mg) was dissolved in dichloromethane (5 ml) and 1-dodecanethiol (0.06 ml) was added. The solution was stirred at room temperature for 7 hours. Removal of the solvent gave a yellow solid which was then recrystallised from absolute ethanol to give 1,8-dihydroxy-10-dodecylthio-9-anthrone (89 mg, 85%) as pale yellow needles, melting point 76° C.

(Found: C 73.3, H 8.2, S 7.9; C$_{26}$H$_{34}$O$_3$S requires C 73.2, H 8.05, S 7.5%).

Physical properties measured:

delta (CDCl$_3$, 220 MHz) 0.83 (t, J=7, —CH$_3$), 1-1.35 (m, —(CH$_2$)$_{10}$—), 2.13 (t, J=7, —SCH$_2$—), 5.14 (s, H-10), 6.90 (d, J=8.3, H-2+H-7), 7.09 (d, J=7.5, H-4+H-5), 7.49 (t, J=8, H-3+H-6), 12.1 (s, 1—OH+-8—OH);

nu max. (film), 2919s, 2848s, 1629vs, 1610vs, 1601vs, 1484s, 1468s, 1448s, 1367m, 1277vs, 1217s, 1069w, 836sh, 750vs cm$^{-1}$; and m/z EI 426 (M+, 1.8), 402(1.3), 256(3.4), 226(49.7), 225(100), 198(9.5), 197(29.1).

EXAMPLE 5

Preparation of 10-(Carboxymethylthio)-1,8-Dihydroxy-9-Anthrone.

(a) 10-Bromo-1,8-dihydroxy-9-anthrone (305 mg) was dissolved in dichloromethane (10 ml) and mercaptoacetic acid (0.07 ml) was added. The solution was stirred at room temperature for 3 days, during which time a yellow precipitate was formed, which was filtered off and recrystallised from absolute ethanol to give 10-(carboxymethylthio)-1,8-dihydroxy-9-anthrone (237 mg, 75%) as yellow needles, melting point 151°-152° C.

(Found: C 60.9, H 3.8, S 10.1%; M=316.0410; C$_{16}$H$_{12}$O$_5$S requires C 60.75, H 3.8, S 10.1%, M=316.0405).

Physical properties measured:

delta (CDCl$_3$, 220 MHz) 3.1 (s, —SCH$_2$—), 5.42 (s, H-10), 7.01 (d, J=8.5, H-2+H-7), 7.14 (d, J=7.5, H-4+H-5), 7.57 (t, J=8, H-3+H-6), 12.12 (s, 1—OH+-8—OH);

nu max. (film), 2960b, 1702s, 1629sh, 1615s, 1602vs, 1481m, 1446s, 1367s, 1274vs, 1218vs, 1185s, 1071m, 919m, 834sh, 779sh, 728vs cm$^{-1}$; and m/z EI 316 (M+, 4.1), 256(14), 241(15), 240(10.8), 238(9.7), 227(15.8), 226(100), 225(82.2), 198(16.5), 197(47.4), 169(6.6), 92(28.2).

(b) A 5% sodium hydroxide solution (6 ml) was purged with nitrogen for 10 minutes, 10-(methoxycarbonylmethylthio)-1,8-dihydroxy-9-anthrone (60 mg) was then added. The solution was stirred at room temperature for 10 minutes under nitrogen. The red brown solution was then diluted with water (10 ml) and neutralised with 10% hydrochloric acid to form the product as a pale brown precipitate, which was extracted with chloroform (15 ml). The organic layer was then washed with water and dried over sodium sulphate. Removal of the solvent and recrystallisation of the residue from ethanol gave 10-(carboxymethylthio)-1,8-dihydroxy-9-anthrone (41.3 mg, 72%) as yellow needles, melting point 150°-152° C.

EXAMPLE 6

Preparation of 10-(Carboxyethylthio)-1,8-Dihydroxy-9-Anthrone.

(a) 10-Bromo-1,8-dihydroxy-9-anthrone (305 mg) was dissolved in dichloromethane (10 ml) and 3-mercaptopropionic acid (0.09 ml) was added. The solution was stirred at room temperature for 3 days, during which time a yellow precipitate was formed. This precipitate was filtered off and recrystallised from absolute ethanol to give 10-(carboxyethylthio)-1,8-dihydroxy-9-anthrone (240 mg, 72.7%) as pale yellow needles, melting point 152°-15° C.

(Found: C 61.5, H 4.3, S 9.8%; M=330.0548; C$_{17}$H$_4$O$_5$S requires C 61.8, H 4.3, S 9.7%; M=330.0562).

Physical properties measured:

delta (CDCl$_3$, 220 MHz) 2.27 (t, J=7.2, 1×CH$_2$), 2.48 (t, J=7.2, 1×CH$_2$), 5.24 (s, H-10), 6.97 (d, J=8.2, H-2+H-7), 7.13 (d, J=7.8, H-4+H-5), 7.54 (t, J=8, H-3+H-6), 12.13 (s, 1—OH+8—OH);

nu max. (film), 2933b, 1694m, 1659w, 1626s, 1598vs, 1482m, 1448m, 1412m, 1366sh, 1273s, 1214vs, 1155s, 1070m, 921w, 836sh, 755vs, 736s cm$^{-1}$; and m/z EI 330 (M+, 6.5), 256(5.8), 240(1.6), 227(7.9), 226(51.3), 225(100), 198(17.9), 197(70.6), 169(9.3), 106(27.3).

(b) A 5% sodium hydroxide solution (5 ml) was purged with nitrogen for 10 minutes, and 10-(methoxycarbonylethylthio)-1,8-dihydroxy-9-anthrone (50 mg) was then dissolved in it at room temperature under nitrogen The red-brown solution was then immediately diluted with water (10 ml) and neutralised with 10% hydrochloric acid to form the desired acid as a pale brown precipitate. The product was then extracted with chloroform (15 ml), washed with water and dried over anhydrous sodium sulphate. Removal of the solvent and recrystallisation of the residue from ethanol gave 10-(carboxyethylthio)-1,8-dihydroxy-9-anthrone (33 mg, 69%) as yellow needles, melting point 150°-152° C.

EXAMPLE 7

Preparation of
10-(Methoxycarbonylmethylthio)-1,8-Dihydroxy-9-Anthrone.

10-Bromo-1,8-dihydroxy-9-anthrone (100 mg) was dissolved in dichloromethane (7 ml) and methyl thioglycollate (0.03 ml) was added. The red-brown solution became yellow-green on addition of the thiol. The solution was stirred at room temperature for 4 hours, after which time the solvent was removed to give a pale green solid (110 mg) which, by recrystallisation from hexane, gave 10-(methoxycarbonylmethylthio)-1,8-dihydroxy-9-anthrone (92 mg, 85%) as yellow needles, melting point 120°-122° C. (with decomposition).

(Found: C 61.9, H 4.3, S 9.5%; $C_{17}H_4O_5S$ requires C 61.8, H 4.3, S 9.7%).

Physical properties measured:

delta ($CDCl_3$, 220 MHz) 2.99 (s, —$SCH_2$—), 3.59 (s, OMe), 5.35 (s, H-10), 6.95 (d, J=8.5, H-2+H-7), 7.09 (d, J=7.5, H-4+H-5), 7.51 (t, J=8, H-3+H-6), 12.08 (s, 1—OH+8—OH);

nu max. (film), 3040b, 1736s, 1631s, 1612vs, 1601vs, 1484s, 1448vs, 1369m, 1278w, 1222s, 1166m, 1073sh, 922w, 837sh, 741s cm$^{-1}$; and m/z EI 330 (M+, 10.3), 257(2.8), 256(7.6), 226(41.4), 225(100), 197(30.5), 169(3.7), 151(10.7), 106(12.3).

EXAMPLE 8

Preparation of
10-(Methoxycarbonylethylthio)-1,8-Dihydroxy-9-Anthrone.

10-Bromo-1,8-dihydroxy-9-anthrone (122 mg) was dissolved in dichloromethane (8 ml) and then methyl 3-mercaptopropionate (0.05 ml) was added. The red-brown solution became yellow-green immediately after addition of the thiol. The solution was stirred at room temperature for 5 hours. Removal of the solvent and recrystallisation of the residue from hexane gave the product (107.5 mg, 78%) as yellow needles, melting point 92°-94° C. (with decomposition).

(Found: C 62.9, H 4.7, S 9.4%; $C_{18}H_{16}O_5S$ requires C 62.8, H 4.7, S 9.3%).

Physical properties measured:

delta ($CDCl_3$, 220 MHz) 2.23 (t, J=7, 1×$CH_2$), 2.50 (t, J=7, 1×$CH_2$), 3.62 (s, OMe), 5.23 (s, H-10), 6.97 (d, J=8.5, H-2+H-7), 7.13 (d, J=7.5, H-4+H-5), 7.55 (t, J=8, H-3+H-6), 12.12 (s, 1—OH+8—OH);

nu max. (film), 2997b, 1735vs, 1629s, 1612s, 1600vs, 1483s, 1450s, 1369m, 1274vs, 1213vs, 1153m, 1073sh, 838sh 762vs 737s cm$^{-1}$; and m/z EI 344 (M+, 5.4), 257(2.5), 256(2), 226(33), 225(100), 198(17.3), 197(79), 169(12.2), 168(10.4), 151(36.9), 120(3.4), 119(3.8), 88(8.5), 87(12.5).

EXAMPLE 9

Preparation of
10-(2,3-Dihydroxypropylthio)-1,8-Dihydroxy-9-Anthrone.

10-Bromo-1,8-dihydroxy-9-anthrone (122 mg) was dissolved in dichloromethane (10 ml) and then 3-mercapto-1,2-propanediol (0.04 ml) was added. The solution was stirred at room temperature for 24 hours, during which time a pale yellow precipitate was formed.

Removal of the solvent and recrystallisation of the residue from ethanol gave 10-(2,3-dihydroxypropylthio)-1,8-dihydroxy-9-anthrone (104 mg, 78%) as light yellow needles, melting point 54°-155° C.

(Found: M=332.0707; $C_{17}H_{16}O_5S$ requires M=332.0718.)

Physical properties measured:

delta ($CDCl_3$, 220 MHz) 1.45-1.90 (bs, 2'—OH+-3'—OH), 2.46 (bd, J=5, 2×H-3') 3.30-3.75 (m, 2×H-1'+H-2'), 5.28 (s, H-10), 6.94 (d, J=8.3, H-2+H-7), 7.13 (d, J=7.7, H-4+H-5), 7.58 (t, J=8, H-3+H-6), 12.1 (s, 1—OH+8—OH);

nu max. (film), 3358b, 2921b, 1629s, 1609vs, 1600vs, 1484m, 1449s, 1278vs, 1219s, 1165m, 1073m, 1026w, 924sh, 838sh 744s cm$^{-}$; and m/z EI 332 (M+, 1.3), 257(1), 256(2.6), 240(3), 227(15.1), 226(93.3), 225(39), 198(21.4), 197(37.5), 180(8.9), 152(15.8), 151(14.3), 77(25.6), 76(16.1), 75(18.3), 63(10.7), 61(41), 59(54.2), 58(18.3), 57(100).

EXAMPLE 10

Preparation of
10-(2-Mercaptoethylthio)-1,8-Dihydroxy-9-Anthrone.

10-Bromo-1,8-dihydroxy-9-anthrone (75 mg) was dissolved in dichloromethane (5 ml) and 1,2-ethanedithiol (0.05 ml, 1.1 equivalent was added. The solution was stirred at room temperature for 6 hours. Removal of the solvent gave a pale green solid (80 mg) which was then recrystallised from ethanol to give 10-(2-mercaptoethylthio)-1,8-dihydroxy-9-anthrone (67 mg, 86%) as pale yellow needles, melting point 133°-134° C.

(Found: C 59.7, H 4.4, S 19.6%; M=318.0369; $C_{16}H_{14})_3S_2$ requires C 60.3, H 4.4, S 20.1%; M=318.0384).

Physical properties measured:

delta ($CDCl_3$, 220 MHz) 1.46 (t, J=8.2, —SH), 2.30 (dt, $J_1$=8.2, $J_2$=7.5, —$CH_2SH$), 2.46 (t, J=7:5, —$SCH_2$—), 5.24 (s, H-10), 6.97 (d, J=8.5, H-2+H-7), 7.13 (d, J=7.8, H-4+H-5), 7.54 (t, J=7.8, H-3+H-6), 12.12 (s, 1—OH+8—OH):

nu max. (film), 3031b, 2562b, 1628s, 1597vs, 1483s, 1447s, 1365m, 1274vs, 1205vs, 1158s, 1073sh, 833sh, 761vs cm$^{-1}$; and m/z EI 308 (M+, 6), 316(3.7), 288(2.9), 287(2.7), 258(1.5), 257(3.3), 256(5.3), 227(8.3), 226(58.2), 225(100), 198(11.4), 197(39.8), 181(2.5), 180(3), 169(5.3), 168(4.5), 152(8.3), 151(15.2), 141(8.4), 61(12.7), 60(10.8), 49(19.1), 47(13.8).

EXAMPLE 11

Preparation of
10-(2-Hydroxyethylthio)-1,8-Dihydroxy-9-Anthrone.

10-Bromo-1,8-dihydroxy-9-anthrone (100 mg) was dissolved in dichloromethane (7 ml) and 2-mercaptoethanol (0.03 ml) was added. The solution was stirred at room temperature for 7 hours, during which time the light brown solution became pale green. Removal of the solvent and recrystallisation of the residue from a hexane/chloroform mixture (5:1) gave 10-(2-hydroxyethylthio)-1,8-dihydroxy-9-anthrone (89 mg, 90%) as pale yellow needles, melting point 146°-147° C.

(Found: C 63.1, H 4.75, S 10.7; $C_{16}H_{14}O_4S$ requires C 63.55, H 4.7, S 10.6%).

Physical properties measured:

delta ($CDCl_3$, 220 MHz) 1.68 (bs, 2'—OH), 2.42 (t, J=6, 1×$CH_2$), 3.38 (t, J=6, 1×$CH_2$), 5.26 (s, H-10), 6.95 (d, J=8.5, H-2+H-7), 7.14 (d, J=7.8, H-4+H-5), 7.53 (t, J=8, H-3+H-6), 12.11 (s, 1—OH+8—OH):

nu max. (film), 3364b, 1627s, 1598vs, 1481s, 1448s, 1365m, 1334m, 1272vs, 1214vs, 1155s, 1072s, 1026m, 922sh, 837sh, 804w, 752vs cm$^{-1}$; and m/z EI 302 (M$^+$, 7.4), 257(2), 256(3.1), 240(2.9), 227(6.7), 226(48), 225(100), 198(9.2), 197(35), 169(4.3), 168(3.30, 152(6.5), 151(11.7), 78(6.9), 76(6.5), 48(10.8), 47(15.6), 46(4).

EXAMPLE 12

Preparation of 1,2-Bis-(1,8-Dihydroxy-9-Anthron-10-ylthio)-Ethane.

10-Bromo-1,8-dihydroxy-9-anthrone (122 mg) was dissolved in dichloromethane (10 ml) and 1,2-ethanedithiol (0.017 ml) was added. The solution was stirred at room temperature for 24 hours, during which time the product precipitated out. Filtration and recrystallisation of the residue from diethyl ether gave 1,2-bis-(1,8-dihydroxy-9-anthron-10-ylthio)-ethane (113 mg, 80%) as pale yellow needles, melting point 186°-187° C.

Physical properties measured:

delta (CDCl$_3$, 300 MHz) 2.05 (s, —SCH$_2$CH$_2$S—), 5.12 (s, 2×H-10), 6.95 [d, J=8.4, 2×(H-2+H-7) or 2×(H-4+H-5)], 7.03 [d, J=7.5, 2×(H-4+H-5) or 2×(H-2+H-7)], 7.50 [t, J=8, 2×(H-3+H-6)], 12.13 (s, 2×1—OH+2×8—OH);

nu max. (film), 3340b, 1625s, 1597vs, 1479s, 1447s, 1418m, 1333m, 1269vs, 1215vs, 1153s, 1069s, 921sh, 754vs, 711s cm$^{-1}$; and m/z EI 316 [(M-Anthralin)$^+$, 13], 288(10.5), 287(14.5), 256(17), 240(17), 228(6), 227(15.5), 226(100), 198(14), 197(19.5), 180(6), 152(16.5), 139(12.5), 115(12.5), 84(20.5), 76(16), 60(24), 59(25.5), 58(23), 57(9), 46(8.5), 45(31.5).

EXAMPLE 13

Addition oil Phenyl Isocyanate to 10-(2-Mercaptoethylthio)-8-Dihydroxy-9-Anthrone.

10-(2'-Mercaptoethylthio)-1,8-dihydroxy-9-anthrone (30 mg) was dissolved in dichloromethane (10 ml), and then silica gel powder (0.5 g) and phenyl isocyanate (8 drops) were added. The mixture was stirred at room temperature overnight. Filtration and removal of the solvent gave an orange yellow solid (40 mg). Washing this with a hexane/chloroform mixture (1:1, 2 ml) gave N-phenyl—S—(1,8-dihydroxy-9-anthron-10-ylthioethyl)thiocarbamate (33.8 mg, 82%) as yellow needles, melting point 144°-146° C.

(Found: C 62.3, H 4.4, S 14.25; C$_{23}$H$_{19}$NO$_4$S$_2$ requires C 63.15, H 4.4, S 14.6%).

Physical properties measured:

delta (CDCl$_3$, 220 MHz) 2.50-2.62 (m, part of AA'BB' system[3], J$_{AB}$+J$_{AB'}$=15, 1×CH$_2$), 2.80-2.93 (m, part of AA'BB' system, J$_{BA}$+J$_{BA'}$=15, 1×CH$_2$), 5.28 (s, H-10), 6.95 (d, J=8.3, H-2+H-7 or H-4+H-5), 7.02 (bs, removed with D$_2$O, NH), 7.15 (d, J=7.7, H-4+H-5 or H-2+H-7), 7.28-7.45 (m, -Ph), 7.52 (t, J=7.9, H-3+H-6), 12.14 (s, 1—OH+8—OH);

delta (CDCl$_3$, 300 MHz) 2.54-2.64 (m, J$_{AB}$+-J$_{AB'}$=15, 1×CH$_2$), 2.85-2.95 (m, J$_{BA}$+J$_{BA'}$=15, 1×CH$_2$), 5.29 (s, H-10), 6.97 (d, J=8.5, H-2+H-7 or H-4+H-5), 6.99 (bs, removed by D$_2$O, NH), 7.17 (d, J=7.5, H-4+H-5 or H-2+H-7), 7.32-7.48 (m, -Ph), 7.53 (t, J=8, H-3+H-6), 12.20 (s, 1—OH+8—OH); and nu max. (film), 3308b, 3040b, 1631s, 1599vs, 1535s, 1485s, 1445vs, 1369w, 1279s, 1225s, 1157s, 1074w, 881w, 837sh, 751s, 693sh cm$^{-1}$; and m/z EI 437 (M$^+$, 0.5), 318(0.8), 317(0.8), 316(4), 288(2.7), 287(2.9), 256(11), 227(33), 226(82.5), 225(62.5), 198(38), 197(64.5), 152(34), 151(32.5), 120(49), 119(100), 93(15), 92(31), 91(87), 77(22), 65(50), 64(92), 63(67).

The 10-bromo-1,8-dihydroxy-9-anthrone required for the above procedures may be made as follows:

1,8-Dihydroxy-9-anthrone (17.3 g) was dissolved in carbon disulphide (1.25 liter) by heating, and the solution was treated dropwise with 18.5 g of bromine with stirring at 50° C. The solution was left stirring at that temperature overnight, then cooled to room temperature and concentrated to one tenth of its volume by removal of the solvent under reduced pressure. The yellow precipitate was filtered off, dried and recrystalised from a petroleum ether (boiling point 40°-60° C.)/chloroform mixture (1:1) to give 10-bromo-1,8-dihydroxy-9-anthrone (18.1 g, 77.5%), melting point 149°-15° C. (with decomposition). [Literature reference, O. E. Schultz and H.-H. Schultze-Mosgau, *Arch. Pharm.* (*Weinheim, Ger.*), 1965, 298, 273, gives melting point 148°-150° C. (with decomposition)].

EXAMPLE 14

Preparation of 1,8-Dihydroxy-9,10-Anthracenedione-10-Ethylenethioketal.

10-(2-Mercaptoethylthio)-1,8-dihydroxy-9-anthrone (48.7 mg) was dissolved in dichloromethane (10 ml) and the solution was purged with nitrogen for 10 minutes. 2,3-Dichloro-5,6-dicyano-1,4-benzoquinone (34.05 mg) was then added and the solution was stirred at room temperature for 17 hours under nitrogen, during which time a white precipitate of 2,3-dichloro-5,6-dicyano-1,4hydroquinone was formed.

Filtration and removal of the solvent gave a dark green solid, which was shown by pmr spectroscopy in CDCl$_3$ to be a mixture (approx. 3:1) of 1,8-dihydroxy-9,10-anthracenedione-10-ethylenethioketal (delta 12.29, 2×OH) and 1,1',8,8'-tetrahydroxy-10,10'-dianthrone (delta 11.57, 4×OH). The mixture was extracted with hot hexane (20 ml). Removal of the solvent gave a yellow solid (33 mg) which was then recrystallised from hexane to give 1,8-dihydroxy-9,10-anthracenedione-10-ethylenethioketal (24.8 mg, 51.5%) as yellow needles, melting point 197°-199° C.

(Found: C 60.65, H 3.8, S 20.5%; C$_{16}$H$_{12}$O$_3$S$_2$ requires C 60.7, H 3.8, S 20.3%).

Physical properties measured:

delta (CDCl$_3$, 220 M8z) 3.74 (s, 2×CH$_2$), 6.94 (dd, J$_1$=8.2, J$_2$=1.1, H-2+H-7 or H-4+H-5), 7.51 (t, J=8.2, H-3+H-6), 7.72 (dd, J$_1$=7.9, J$_2$=1.1, H-4+H-5 or H-2+H-7), 12.57 (s, 1—OH+8—OH);

nu max. (film), 2850b, 1631vs, 1596vs, 1570m, 1478s, 1441s, 1376m, 1332m, 1296s, 1274s, 1256s, 1208s, 1168m, 1156m, cm$^{-1}$; and 1079w, 849sh, 796sh, 750vs, 718s cm$^{-1}$; and m/z EI 316 (M$^+$, 100), 289(15.7), 288(64.9), 287(65.6), 271(21), 257(16.9), 256(78.1), 228(17.1), 226(8.3), 200(4.9), 182(5.3), 171(7.9), 139(6.3).

EXAMPLE 15

Preparation of 1,8-Dihydroxy-9,10-Anthracenedione-10-Ethylenehemithioketal.

10-(2-Hydroxyethylthio)-1,8-dihydroxy-9-anthrone (30.2 mg) was dissolved in dichloromethane (5 ml) and the solution was purged with nitrogen for 10 minutes. 2,3-Dichloro-5,6-dicyano-1,4-benzoquinone (22.7 mg) was then added and the solution was stirred at room temperature for 15 hours under nitrogen, during which time a white precipitate of 2,3-dichloro-5,6-dicyano-1,4-hydroquinone was formed.

Filtration and removal of solvent gave an orange-brown solid, which was recrystallised from hexane to give 1,8-dihydroxy-9,10-anthracenedione-10-ethylenehemithioketal (25 mg, 75%) as orange-yellow needles, melting point 165°–166° C.

(Found: C 64.2, H 4.05, S 10.7%; $C_{16}H_{12}O_4S$ requires C 64, H 4, S 10.7%).

Physical properties measured:

delta ($CDCl_3$, 220 MHz) 3.37 (t, J=5.7, —$OCH_2$—), 4.79 (t, J=5.7, —$SCH_2$—), 6.96 (dd, $J_1$=8.5, $J_2$=1.2, H-2+H-7 or H-4+H-5), 7.16 (dd, $J_1$=8, $J_2$=1.2, H-4+H-5 or H-2+H-7), 7.52 (t, J=8.2, H-3+H-6), 12.01 (s, 1—OH+8—OH);

nu max. (film), 3072b, 1631s, 1608vs, 1601vs, 1573m, 1476s, 1445s, 1361w, 1265vs, 1215s, 1164s, 1077sh, 816m, 766m, 745m cm$^{-1}$; and m/z EI 300 (M+, 8.5), 241(16.2), 240(100), 223(5.2), 212(16.5), 184(13.8), 155(4.2), 138(6.4).

EXAMPLE 16

Cyclisation of 10-(Carboxymethylthio)-1,8-Dihydroxy-9-Anthrone.

10-(Carboxymethylthio)-1,8-dihydroxy-9-anthrone (55 mg) was dissolved in dichloromethane (8 ml) and the solution was purged with nitrogen for 10 minutes. 2,3-Dichloro-5,6-dicyano-1,4-benzoquinone (39.5 mg) was then added and the solution was stirred at room temperature overnight under nitrogen, during which time a white precipitate of 2,3-dichloro-5,6-dicyano-1,4-hydroquinone was formed.

The solution was filtered and the solvent was removed from the filtrate to give a brown solid, which was extracted with chloroform (3 ml). Filtration and removal of the solvent was followed by extraction of the solid with hot hexane (3×2 ml portions) to give, after crystallisation from hexane, the cyclised product (46 mg, 83%) as a pale brown solid, melting point 140°–155° C. (with decomposition).

(Found: M=314.0276; $C_{16}H_{10}O_5S$ requires M=314.0249).

Physical properties measured:

delta ($CDCl_3$, 220 MHz) 4.05 (s, $CH_2$), 7.02 (dd, $J_1$=8.5, $J_2$=1, H-2+H-7), 7.10 (dd, $J_1$=7.5, J=1, H-4+H-5), 7.57 (t, J=8, H-3+H-6), 11.98 (s, 1—OH+8—OH);

nu max. (film), 3583b, 2250b, 1766s, 1630s, 1599vs, 1573s, 1445vs, 1413s, 1275vs, 1190vs, 1168vs, 1057m, 966s, 811sh, 780sh, 723vs cm$^{-1}$; and m/z EI 314 (M+, 14.3), 268(11.1), 256(10.8), 242(14.4), 241(100), 240(65.8), 239(7.2), 238(23.9), 228(12.2), 212(8.7), 184(8.2).

EXAMPLE 17

Cyclisation of 10-(Carboxyethylthio)-1,8-Dihydroxy-9-Anthrone.

10-(Carboxyethylthio)-1,8-dihydroxy-9-anthrone (40 mg) was dissolved in dichloromethane (7 ml) and the solution was purged with nitrogen for 10 minutes. 2,3-Dichloro-5,6-dicyano-1,4-benzoquinone (27.5 mg) was then added and the solution was stirred at room temperature overnight under nitrogen, during which time a white precipitate of 2,3-dichloro-5,6-dicyano-1,4-hydroquinone was formed.

The solution was filtered and the solvent was removed from the filtrate to give a brown solid which, by extraction with chloroform (2 ml), filtration and removal of the solvent gave a solid which was washed with hexane (3×2 ml portions) to give the cyclised product (32 mg, 80%) as a pale brown solid, melting point 150°–15° C. (with decomposition).

Physical properties measured:

delta ($CDCl_3$, 220 MHz) 2.35 (t, J=6, 1×$CH_2$), 3.08 (t, J=6 1×$CH_2$), 7.01 (d, J=8.3, H-2+H-7 or H-4+H-5), 7.06 (d, J=8.5, H-4+H-5 or H-2+H-7), 7.57 (t, J=8.3, H-3+H-6), 11.95 (s, 1—OH+8—OH);

nu max. (film), 2915b, 2850b, 1710s, 1670vs, 1601vs, 1574s, 1463s, 1445s, 1274vs, 1208s, 1161s, 843sh, 720vs cm$^{-1}$; and m/z EI 328 (M+, 2.1), 257(1.6), 256(8), 241(19.8), 240(100), 228(4,9), 212(7.4), 184(7.2).

The cyclised product produced in Example 16 is Spiro[3-thia-gamma-butyrolactone-4,10-1',8'-dihydroxy 9'-anthrone].

The cyclised product produced in Example 17 is Spiro[4-thiadelta-valerolactone-5,10-1',8'-dihydroxy-9'-anthrone].

I claim:

1. Process for the manufacture of a compound of the formula I

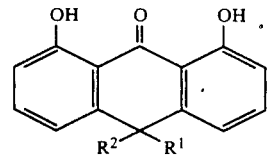

wherein $R^1$ represents the substituent —SR, wherein R represents substituted or unsubstituted alkyl of 1 to 12 carbon atoms or a substituted group; or unsubstituted aryl and $R^2$ represents hydrogen or $R^1$ (in which case the two groups R therein may be the same or different), which comprises reaction between a thiol and an anthralin containing a substituent which is reactive with a thiol in the 10-position to form a thio linkage.

2. Process for the manufacture of a compound of the formula (I) in claim 1 which comprises interacting a reactive derivative of anthralin and a compound which contains a group which is convertible to a thio-substituent.

3. Process as claimed in claim 1 or claim 2, wherein the product is a 10-substituted anthralin, and the reaction comprises interacting a 10-halogenated anthralin and a thiol or a compound which contains a group which is convertible to a thio-group.

* * * * *